United States Patent [19]

Chang

[11] Patent Number: 5,037,384
[45] Date of Patent: Aug. 6, 1991

[54] METHOD AND APPARATUS FOR THE TREATMENT OF COMPLICATED RETINAL DETACHMENTS

[75] Inventor: Stanley Chang, Scarsdale, N.Y.
[73] Assignee: Cornell Research Foundation, Inc., Ithaca, N.Y.
[21] Appl. No.: 405,615
[22] Filed: Sep. 11, 1989

Related U.S. Application Data

[63] Continuation of Ser. No. 142,614, Jan. 12, 1988, abandoned.

[51] Int. Cl.$^5$ ............................................... A61M 1/00
[52] U.S. Cl. ........................................ 604/28; 604/49
[58] Field of Search ................... 604/22, 28, 49, 51

[56] References Cited

U.S. PATENT DOCUMENTS 4,490,351 12/1984 Clark, Jr. .
4,795,423 1/1989 Osterholm ............................ 604/51

FOREIGN PATENT DOCUMENTS 8701271 3/1987 PCT Int'l Appl. .................. 604/22

OTHER PUBLICATIONS

Some of the Most Important Properties of Silicone Oil to Explain Its Action, Haut et al, Opthalmologica, Basel, 191: 150–153 (1985).

Primary Examiner—Randall L. Green
Assistant Examiner—K. Reichle
Attorney, Agent, or Firm—Yahwak & Associates

[57] ABSTRACT

The present invention relates to an improved microsurgical instrumentation, and an improved method using a perfluorocarbon material for hydrokinetic manipulation, for the surgical treatment of complicated retinal detachments of the eye.

10 Claims, 1 Drawing Sheet

METHOD AND APPARATUS FOR THE TREATMENT OF COMPLICATED RETINAL DETACHMENTS

This is a continuation of application Ser. No. 142,614, filed 12th Jan. 1988 now abandoned.

This invention relates generally to a novel method for the treatment of complicated retinal detachments and, more specifically to a surgical technique for (1) the unfolding of the retinal flap, (2) the removal enhance of epiretinal membrane and (3) providing minimal posterior slippage of the retinal flat during the surgical repair of giant retinal tears, and (4) exposing the periretinal membranes, (5) displaying the tractional relationships between the retinal membrane and the underlying choroid membranes, (6) providing temporary mechanical fixation of the retinal membrane, (7) providing acceptable ocular tamponade and (8) providing for the displacement of subretinal fluid or blood from the macular area of the eye during the surgical repair of proliferative vitreoretinopathy. This invention also relates to instrumentation for the administration of liquids to the interior of the ocular globe during surgical procedures.

Retinal detachment results generally from the liquefication of the vitreous gel filling the posterior chamber of the eye between the retina and the crystalline lens, and the subsequent separation of this gel from the retinal surface. In a healthy individual, this gel functions to give shape to the eye, aid in the transmission of light from the lens to the retina, and provide a semisolid support to maintain the retina against the choroidal tissues. As one ages or undergoes certain ocular pathologies, however, this gel may become liquified at the retinal interface and subsequently pull away from the retina. If the vitreous gel should separate with sufficient retinal traction, a retinal break or tear may result. Continued traction of the retinal break results in the passage of fluid vitreous through the retinal break and under the retina resulting in retinal detachment. This disorder results in partial or total blindness.

In most cases, a retinal detachment is managed with a surgical procedure referred to as scleral buckling. During this procedure the retinal breaks are localized, subretinal fluid which has found its way across the retinal membrane through the break is drained, and the areas of the retinal tear are supported externally by a silicone element which is sutured to the wall of the eye causing an indentation. There are, however, more severe forms or retinal detachment which require special consideration and a modified approach. It is because of these complicated forms of retinal detachment that the method and apparatus of the present invention are needed.

Retinal detachment may be accompanied by proliferation of abnormal fibrovascular tissue on the surface of the retina forming membranes which result in traction on the surfaces of the retina and prevent successful retinal attachment. These conditions are seen in diabetric retinopathy, proliferative vitreoretinopathy, retinopathy of prematurity, and following ocular trauma. Another form of complicated retinal detachment is the giant retinal tear which results from a large tear in the peripheral retina extending for more than 90 degrees of the eye's circumference.

In these specialized forms of complicated retinal detachment, the vitreous is removed surgically with a cutting and suction instrument following the accepted closed or pars plana technique first described by Machemer et al (see "Vitrectomy: a pars plana approach", Trans Am Acad Opthaomol Otolaryngol 75:813, 1971, and "A new concept of vitreous surgery:Instrumentation", Am J Ophthalmol 73:1, 1972). An earlier technique developed by Kasner et al (see "Surgical treatment of amyloidosis of the vitreous", Trans Am Acad Ophthalmol Otolaryngol 72:410, 1968, and "Vitrectomy:a new approach to the management of vitreous", Highlights Ophthalmol 11:304, 1968) in which the lens of the eye is removed and the vitreous removed through the pupil is also being practiced by ocular surgeons. In both of these procedures, membranes from the surface of the retina are dissected and removed, or traction is released by cutting the membranes. Occasionally, if the traction between the retina and the vitreous cannot be released, the retina must be cut from the area of fibrosis by a procedure called retinotomy.

During vitreous surgery, the abnormal vitreous is removed and replaced by a balanced saline solution. After removal of any membranes on the surface of the retina and the mobility of the retina is regained, sterile air (the procedure favored most in the United States) or silicone oil (the procedure favored most in Europe) is injected into the posterior chamber of the eye to flatten the retina against the choroidal tissues. As both of these vitreous substitutes have lower specific gravity than water, they tend to float on water and fill the anterior portion of the eye first. Most retinal breaks are located in the anterior portion of the eye, and subretinal fluid may be confined under the posterior retina as the injection of the vitreous substitute is made by the surgeon. When subretinal fluid is trapped posteriorly under the retina, an incision through the retina must be made (referred to as a posterior retinotomy) in order to aspirate the subretinal fluid completely and cause the flattening of the retina against the choroid. This surgically necessitated perforation in the retina further damages the retina and may also be a source of potential complications such as bleeding or reproliferation of fibrous tissue. At the completion of the operation, a gas bubble or silicone oil is left in the eye's chamber to provide an internal tamponade force holding the retina in place while laser or cryotherapy scars are formed by the surgeon to provide a permanent chorioretinal adhesion. The interfacial tension of these substances prevent the vitreous substitute from passing through a retinal break and into the subretinal space. Postoperatively, as the patient becomes ambulatory, the silicone or gas bubble will rise to the uppermost portions of the eye (clinically it has been observed that most reccurrences of proliferation occur in the inferior portion of the retina which is not tamponaded by the vitreous substitute). Patients with gas bubbles are instructed to keep their head in the prone position to minimize the complications of surgery such as cataract, angle closure glaucoma, or corneal edema, and similarly, patients with a silicone oil bubble are instructed not to lie supine as the oil bubble may contact the corneal endothelial layer resulting in corneal swelling, opacity, and ultimately blindness.

Interest in developing a vitreous replacement which has higher specific gravity than water led to the operative technique utilizing fluorosilicon oil. A "heavy" liquid circumvents the problem of posterior compartmentalization of the subretinal fluid as vitreous substitute is injected. When fluorosilicone is injected into the vitreous, it flattens the retina posteriorly and displaces the subretinal fluid anteriorly through the retinal tear.

All silicon oils were developed for long-lasting replacement of the vitreous for periods ranging from three months or longer. These substances have significantly long term intolerance by the eye and may result by promoting pathologies such as glaucoma, corneal clouding, or scarring. One of the major disadvantages of presently available silicone oils is their inherent high viscosities, ranging from 1,000 to 12,500 centistokes, which makes it difficult for the surgeon to inject and to remove the liquid through microsurgical instrumentation required for vitrectomy. Thus, science has continued to pursue an acceptable liquid material which has higher specific gravity, and one which can be easily introduced and removed from the eye during surgery for the manipulation of the detached retina. Until the present invention, the liquids and techniques for their use had not been previously known.

Recently, liquid perfluorocarbons have also been investigated as possible long-term replacements for vitreous. Clark (U.S. Pat. No. 4,490,351), for example, proposed the use of perfluorocarbons for intraocular use when injected into the cornea, lens or vitreous. He did not, however, consider the use of liquid perfluorocarbons as an adjunct to the surgical manipulation during vitrectomy, as is done in the present invention. It was not long before the utility of the techniques and materials described by Clark became criticized for their scientific merit based upon investigations conducted at the Eye Research Institute of Retina Foundation and at the Harvard Medical School (see, for example, Miyamoto et al, "Perfluoroether liquid as a long-term vitreous substitute", RETINA 4:264–268, 1984, and Miyamoto et al, "Fluorinated oils as experimental vitreous substitutes", Arc Ophthalmol 104:1053–1056, 1986). The use of perfluorocarbons as long-term replacements for vitreous is not medically acceptable, contrary to what is described in the Clark patent, and may, in many instances, cause additional damage to the eye including permanent blindness.

The investigations which resulted in the making of the present invention have now show that low viscosity liquid perfluorocarbons may not be medically sound as long-term vitreous replacements, but that these compounds have the low viscosity, high density, and desirable interfacial tension properties which would make them ideal for use as an intraoperative tool during vitreous surgery for complicated retinal detachments, so long as the liquid perfluorocarbon is removed at the end of the reattachment.

By "vitreous surgery for complicated retinal detachments" is meant, according to the present invention, those surgeries during which it may become necessary to perform various manipulations of the retina such as peeling of membranes, sectioning of membranes, or unfolding the retina in a giant retinal tear. Furthermore, as gases or "light" silicone oil is injected into the eye, a giant retina tear may slip posteriorly and not reattach in a smooth layer. In order to provide fixation of the retina so that this posterior slippage does not occur, various procedures such as retinal incarceration, transretinal suturing, or retinal tacks have been used to mechanically fix and hold th retina in place. These procedures intrinsically may cause damage to the retina and may result in extensive bleeding which would further reduce the chances of successful surgery. When air or other gases are used intraoperatively, visualization of the retina is difficult because of optical changes induced by the difference in indices of refraction at the bubble interface. The use of silicone oil improves visualization compared with gas, but dissection of membranes is usually performed against the oil bubble which may result in migration of oil under the retina. Sodium hyaluronate 1% (the only vitreous replacement presently used in vitreous surgery that is denser than saline) has also been used as an intraoperative adjunct during vitreous surgery, however, its specific gravity (1.036) and low interfacial tension and undesirable physical characteristics. Furthermore, the high viscosity (200,000 centistokes) of this material makes it difficult to inject and aspirate this material with the small microsurgical instruments required in ocular surgery.

Thus, a useful intraoperative tool which could displace subretinal fluid, provide temporary mechanical fixation of the retina, and allow dissection of membranes or positioning of the retina would be extremely valuable to the ophthalmic surgeon. The more effectively that scar tissue can be removed, with accurate reattachment of the retina, the greater the chance that vision would be restored to the fullest extent. The present invention describes such an intraoperative tool.

According to the present invention, low viscosity liquid perfluorocarbons and substituted derivatives of these perfluorocarbons have been found to be useful as an intraoperative tool during vitreous surgery for the manipulation of the retina. These materials all share the characteristic of being optically clear and having a higher specific gravity than water (thereby allowing the fluid to hydraulically push the retina back into place and to displace the subretinal fluid anteriorly through preexisting retinal breaks). The force, for example, exerted by 5 ml of perfluorotributylamine (one of the compounds having use in the present invention) against the retina is 4.3 grams; compared with other vitreous substitutes, this force is greater than that exerted by an equivalent volume of silicone oil (0.3 grams) or fluorosilicone oil (1.35 grams), but less than that of air of gases (5.15 grams). The low viscosity of these fluids allows easy injection and removal through microsurgical instruments. The liquids are immiscible with water and blood, and therefore provide a clear optical pathway during intraoperative bleeding. Their interfacial tension properties prevent the displacement of fluid through small retina tears into the subretinal space. The liquid perfluorocarbon is removed at the end of the surgery, a procedure made relatively easy by the low viscosity of these materials, and replaced by the long-term vitreous substitute chosen by the surgeon.

Another aspect of the perfluorocarbons according to the present invention involves the use of low viscosity perfluorocarbons which are normally liquid at room temperature but which assume a gaseous phase (at body temperature) when injected into the eye. This aspect allows for the injection of a small amount of a liquid species into the eye which subsequently vaporizes and transforms itself into a gas bubble to provide the needed intraocular tamponade at the conclusion of the surgery.

Still another aspect of the present invention is a single use, disposal microsurgical instrument which functions as a carpel containing the sterile liquid perfluorocarbon to be used during surgery, a dispensing apparatus for injecting the sterile material into the cavity of the eye.

The advantages of utilizing liquid perfluorocarbon compounds in the surgical correction of giant retina tears include:
aiding in the unfolding of the giant retinal tear;
enhancing the removal of the epiretinal membranes;

minimizing posterior slippage of the retinal flap;
allowing cryotherapy or photocoagulation to take place with the retina still in place thus minimizing dispersion of potentially proliferating cells; and
the patient is able to remain supine throughout the operation.

The advantages of utilizing liquid perfluorocarbon compounds in the surgical correction of proliferative vitreoretinopathy include
allowing for the exposure of periretinal membranes;
allowing for the display of tractional relationships;
providing for the temporary mechanical fixation required for successful vitreous bas dissection, retinotomy, and retina tack insertion; and
allowing for the displacement of subretinal fluid/blood with the need for posterior retinotomy.

The perfluorocarbons (compounds consisting of carbon atoms fully saturated with fluorine atoms, including cyclic as well as non-cyclic species) and any substituted perfluorocarbon derivatives (compounds which are substituted by atoms which do not affect the toxicity of the perfluorocarbon nor give it physical characteristics other than those desired for the purposes of the present invention as, for example, the conventional substitution of a nitrogen atom for one of the fluoride moieties in order to link or polymerize two perfluorocarbons together would be considered as one manner of providing a substituted perfluorocarbon derivative under the present invention) which are liquids at room temperature, including mixtures of perfluorocarbons, may be used in the method according to the present invention. Among the compounds which may be used in the present invention are perfluoropentane, perfluorohexane, perfluoroheptane, perfluorooctane, perflorononane, perflorodecaline, perfloromethylcyclohexane, perflorodimethyladamantane, perfloromethyladamantane, perflorodimethylcyclohexane, perflorotributylamine, perflorotripropylamine, and perfloropolyether polymers. The compounds which may be used for the present invention all share similar physical characteristics, specifically they all have a refractive index which ranges from about 1.25 to about 1.34, a specific gravity of about 1.3 to about 2.1, a surface tension of from about 16 to about 22 dynes per centimeter, and a viscosity ranging from about 0.6 to about 30 centistokes at 20 degrees centigrade. Other low viscosity fluorinated compounds having similar physical characteristics to the perfluorocarbons, such as compounds in the family of fluorosilicone oils, may also be used in the present invention.

Another group of perfluorocarbons which may be utilized in the present invention are mixtures of two or more perfluorocarbons which are each in different phases at room temperature. These mixtures would include, for example, perfluorodimethylcyclobutane which is a liquid at room temperature and assumes a gaseous phase at body temperature. This two-phase property has been found to be useful in providing both a gas bubble for superior retina tamponade and a liquid phase for inferior retina tamponade. Similarly, a soluble gaseous perfluorocarbon may be solubilized in a liquid species and when introduced into the vitreous both a gas bubble and a liquid phase will develop. Also similarly, perfluorocarbons which are normally solid at room temperature but become liquid at body temperature, as for example perfluorodecane, may also be used either alone or in combination with other perfluorocarbons in the procedure according to the present invention.

The procedure for the treatment of complicated retinal detachments according to the present invention involves the injection of liquid perfluorocarbons into the eye during vitreous surgery. Although the amount of perfluorocarbons will depend upon the side of the tear or vitreous-retinal attachment, in most instances the amount of liquid injected into the eye would be such that from about 5 to about 85 percent of the eye will become filled with the perfluorocarbon during the operation. The conditions commonly treated as complicated retinal detachments for which this procedure finds a preferred use (although the procedure may also be sued in other, less complicated, ocular surgeries) are complicated retinal detachment secondary to proliferative vitreoretinopathy, proliferative diabetic retinopathy, giant retinal tears, ocular trauma, retinopathy of prematurity, and retinal detachment associated with subretinal hemorrhage. The vitreous in each of these instances is removed mechanically by a vitrectomy instrument and the liquid introduced into the vitreous of the eye over the optic disc after all scar tissue and extraneous membranes are removed in the posterior retina. The liquid then flattens the retina posteriorly opening the funnel of the retina detachment and exposing all remaining membranes on the surface of the retina. As the bolus of liquid is introduced into the eye and flattens the retina, it also stabilizes the retina and provides the mechanical fixation of the retina needed for successful isolation and repair of the retina tear; membranes anterior to the fluorochemical bubble are exposed and able to be dissected and sectioned as required; and any sub-retina fluid is replaced anteriorly through the retinal break without requiring posterior retinotomy. As any unwanted membranes are removed anterior to the bubble of perfluorocarbon introduced into the eye, additional perfluorocarbon is added to the bubble to stabilize the retina. By doing this, additional areas of retinal traction can be relieved by further membrane dissection and sectioning. As an additional benefit of this procedure, the perfluorocarbon bubble also provides additional mechanical fixation for dissection of membranes at the vitreous base. Furthermore, the retina is so stabilized by the temporary mechanical fixation achieved by the perfluorocarbon bubble that a more accurate and limited giant retinotomy can be performed peripherally, if so required, than if this stabilization was lacking. Once the retina is flattened by the liquid perfluorocarbon, laser photocoagulation can be applied (the boiling point of perfluorocarbons exceeds that of saline so that endophotocoagulation can be applied without intraocular vaporiztion) to the retina following conventional procedures. After the retina is fixed to the underlying choroidal tissues, the perfluorocarbon is removed from the eye by aspiration.

In the specific instances of retinal detachment with subretinal blood accumulation, as the perfluorocarbon bubble flattens the retina posteriorly, any accumulation of blood in the subretinal macular area will be displaced. As subretinal blood accumulation is toxic to the photoreceptors of the eye, the displacement of blood out of this region may improve the patient's chances of regaining central or reading vision.

In the instance of giant retinal tears, the liquid perfluorocarbon bubble can unfold the flap, with minimal posterior slippage, of a giant retina tear, and the removal of any epiretinal membranes is enhanced by temporary fixation of the retina by the perfluorocarbon bubble.

Utilizing the procedure of the present invention results in a number of advantages not presently available: retina tacks needed to attach the retina to the underlying tissue, if necessary, may be inserted under the perfluorocarbon while the retina is stabilized by the perfluorocarbon bubble, cyrotherapy or photocoagulation can be applied through the perfluorocarbon bubble thereby minimizing the dispersion of retinal pigment epithelial cells which play a role in the formation of scar tissue on the retina; ocular bleeding is reduced by the tamponade pressure resulting from the bubble (and any blood clot which forms will be held in place by this same pressure); and a further advantage is that the patient remains supine throughout the operative procedure—the patient will not have to be turned into the prone position (reducing the chances of contaminating the operative field and the anesthetic risk), and the surgeon will not have to work from the supine position during the surgery.

At the end of the operation, the perfluorocarbon is removed by aspiration followed by, or concurrently with the introduction of a sterile gas bubble or silicone oil (fluorochemicals are immiscible with the silicone oils, and the two substances form separate phases when mixed) as a longterm vitreous replacement. A novel approach to perfluorocarbon removal from the eye, according to the present invention, involves the introduction into the eye of a small amount of saline to allow residual perfluorocarbon to coalesce into small spheres which can be then individually aspirated to ensure complete removal of the perfluorocarbon. During this fluid-air or fluid-silicone oil exchange, the air-fluorocarbon or fluorocarbon-silicone oil meniscus flattens, resulting in a thin flat layer of residual fluorocarbon oil. This oil is easily removed by injecting into the eye about 0.5 ml to about 0.8 ml of a balanced salt solution. When this is done, the residual fluorocarbon oil forms into small round beads or spheres in the saline, and these can easily be aspirated out of the eye. After complete fluid-air or fluid-silicone oil exchange has taken place, additional endophotocoagulation may be applied to the anterior retina. The vitreous substitute chosen for long-term tamponade as, for example perfluorocarbon gas or silicon oil, is then injected into the air or oil filled eye.

In order to provide a further understanding of the procedure according to the present invention, animal models of retinal detachment were used to evaluate the effectiveness of these perfluorocarbon liquids. In rabbit, pig, and primate eyes the liquid perfluorocarbon mechanically flattened the detached retina effectively. In over 100 rabbit eyes various liquid perfluorocarbons have been injected into the vitreous of the eye in volumes ranging from 1.0 to 1.6 cc. (the rabbit eye volume is approximately 1.6 cc.). In order to create space in the vitreous, a small amount of perfluoropropane gas was injected several days earlier forming a gas bubble which expanded to fill a large volume of the vitreous. When the bubble almost filled the vitreous volume, liquid perfluorocarbon was injected and the gas bubble evacuated. The liquid perfluorocarbons were left in the eye for periods ranging from 24 to 48 hours. Electron microscopy revealed mild photoreceptor toxicity as a result of the liquid perfluorocarbon, however, in animals observed for two or three weeks following removal of the perfluorocarbon, these photoreceptor changes reverted to normal.

The initial short-term experiments in pig and monkey eyes have included the introduction of perfluorotributylamine, perfluorodecalin, and perfluorooctane in the vitreous following virectomy for three hours. Both light and electron microscopy have shown no retina toxic changes when highly purified materials were used.

With the success in animal models, the sue of liquid perfluorocarbons was conducted in human trials. In these patients, medical grade compounds were used for temporary mechanical tamponade during virectomy. Prior to its use, the perfluorocarbon liquids were filtered through two 0.2 um Millipore filters.

CASE I

A ten year old girl was referred with an everted 330 degree giant retinal tear in the right eye. She had undergone lensectomy, vitrectomy, and scleral buckling with sulfur hexafluoride tamponade and cryotherapy two weeks before referral. After an initial success, the retina redetached as the gas bubble resorbed. The rear extended from the 9 o'clock to the 8 o'clock meridians. Fixation of the inferior retina with retinal tacks and silicone oil tamponade were planned for the second procedure. During the operation, the retinal tacking device malfunctioned and extensive bleeding developed from a peripheral retinal vessel. Hemostatis was achieved with endodiathermy. The tear was gently mobilized and sodium hyaluronate was used to try to prevent posterior slippage. Attempts to flatted the tear under gas were unsuccessful because of slippage. Before turning the patient into the prone position for fluid-air exchange, perfluorotributylamine was used. As the liquid was injected over the optic disk and up to the edges of the retinal tear, the retina completely unfolded and flattened. Endophotocoagulation was performed 360 degrees on the buckle through perfluorotributylamine. Fluid air exchange was performed, removing the fluorochemical with the 20-gauge extrusion handpiece. Additional endophotocoagulation was applied anteriorly on the buckle through air. In the air filled eye, silicone oil was injected as the long term tamponade. On the first post-operative day, the retina was completely attached.

CASE II

A mentally retarded 42 year old woman was referred for retinal detachment with proliferative vitreooretinopathy in both eyes. She had a history of self-abuse with gradual loss of ambulatory vision. A retinal detachment associated with a retinal dialysis from the 2 o'clock to the 4 o'clock meridians was found in the left eye. Cyrotherapy, a scleral buckle with drainage of subretinal fluid, and air injection were performed. There was initial successful retinal reattachment. However, eight weeks later the retina redetached because of proliferative vitreoretinopathy.

Extensive posterior synechiae prevented pupillary dilation and a lensectomy was necessary. The retina was totally detached in a closed funnel configuration (Retina Society Classification D3). Periretinal membranes were peeled from the funnel, opening it and increasing retinal mobility centrally. Sodium hyaluronate was injected into the funnel in an attempt to spread open the detachment. However, as the membranes were peeled peripherally, the pulling forces tended to close the funnel. Perfluorotributylamine was then injected over the optic disk flattening the posterior retina until areas of residual traction were visualized. Remaining posterior membranes were better visualized as the retina was held open by the perfluorotributylamine. As additional peripheral membranes were removed, liquid perfluorocarbon was added, which further flattened the retina. Anterior loop traction was released working under the aqueous phase of the vitreous. The retina tear extended from the 1 o'clock to the 4:30 o'clock meridian. As the retina flattened under fluorochemical, a small amount of subretinal hemorrhage initially located around the optic disk and macula was displaced peripherally. The scleral buckle was revised by adding a 289-silicone esoplant along the inferior 180 degrees of the globe. Endophotocoagulation was applied 360 degrees onto the scleral buckle. The retina anterior to the fluorocarbon interface was still partially elevated. Fluid-air exchange was used to flatten the anterior retina while removing the fluorochemical completely. Under air additional endophotocoagulation was administered anteriorly on the buckle. Silicone oil was injected for long-term tamponade because of poor compliance with heat positioning. Two months postoperatively, the retina remains attached.

CASE III

A 23 year old woman was referred for retinal detachment with proliferative vitreoretinopathy in the left eye. After blunt trauma, the patient was treated for retinal detachment with scleral buckling. A retinal dialysis from the 11 o'clock to the 1 o'clock meridians was present. The retina did not flatten and drainage of subretinal fluid with air injection was performed one week later. Four weeks later, a recurrent retinal detachment with proliferative vitreooretinopathy in a narrow funnel configuration (Retinal Society Classification D2) developed.

During surgery dense pigment periretinal membranes were peeled from the retina posteriorly. The retina became mobile as large sheets of membranes were removed to the periphery. No posterior retina breaks were present. To avoid a posterior retinotomy for internal drainage of subretinal fluid, perfluorotributylamine was injected over the optic disk. The retinal funnel opened and flattened, expressing subretinal fluid anteriorly through the retinal tear. The perfluorochemical was injected up to the level of the tear. Anterior membranes were removed when the retina was immobilized by the fluorochemical tamponade. Endophotocoagulation was delivered on the buckle posterior to the tear through the fluorochemical. Fluid-air exchange flattened the anterior retina against the buckle and additional endophotocoagulation was applied 360 degrees anteriorly. At the conclusion of the procedure the air-filled eye was flushed with 20% perfluoropropane-air mixture. The retina has remained attached in this patient for two months.

CASE IV

A 13 year old boy was referred with a giant retinal tear in the right eye. He had undergone cataract aspiration six years earlier for congenital cataract. Subsequently he developed glaucoma. A filtering procedure was performed without complication two weeks before the development of retinal detachment. The superior giant tear extended from the 7:30 o'clock to the 3 o'clock meridians. The tear was everted and immobile with the superior portion of the flap adherent to the inferior retina.

Intraoperatively, the cortical vitreous was removed and the tear gently unfolded with bimanual instrumentation. Five milliliters of perfluorodecaline was infused over the optic disk. The retina immediately unfolded and flattened as the liquid fluorocarbon was injected up to the level of the tear. A broad 3.2×6.4 grooved silicone explant was placed encircling the globe. After placement of the scleral buckle, endophotocoagulation was performed through the perfluorodecaline 360 degrees on the buckle as described above. Photocoagulation was added on the anterior crest of the buckle after fluid-air exchange removed all of the liquid fluorocarbon. At the end of the surgery the retina was completely flattened under air and the eye was flushed with a 20% perfluoropropane-air mixture.

The use of perfluorocarbons in initial animal studies was conducted by placing the liquid perfluorocarbon into a syringe and attaching a hypodermic needle. For injection, the surgeon would introduce the hypodermic needle into the animal's eye, and hold the syringe in place while an assistant would depress the syringe plunger. Since these injections are done in dim light so that the mechanical effects of the perfluorocarbon on retinal flattening can be observed through the operating microscope, and since both the surgeon and an assistant were involved in the dispensing procedure, the surgeon had little control over the amount of liquid injected and often there was a misdirection of the dispensing needle. In order to overcome these disadvantages, and because no company manufactures an acceptable means for dispensing liquid perfluorocarbons into the eye during vitreous surgery, an instrument had to be specially designed and tested. The microinstrumentation necessary to perform the method for the treatment of complicated retinal detachments finally found to be acceptable is also an aspect of the present invention. This instrumentation can be better understood by reference to the accompanying drawings in which:

More specifically, these figures show a hand-held apparatus (10) designed as being generally a conventional transparent cylindrical syringe barrel (11) of glass or plastic construction having a proximal end (12) terminating in a conventional luer lock, and a distal end (13) having conventional outwardly extending flange portions (14) normally used as finger grip means in conventional syringe designs. For ease of manufacture, packaging, and use by the surgeon, it has been found that a 5 or 10 cc. sized syringe barrel is preferred for use in this instrument. As shown, the barrel is sealed at its proximal end by a liquid tight seal means (15) such as a tear cap seal which may be made of any conventionally used sealing material such as paper, foil, or plastic (or combination of these material which is secured by adhesive, heat sealing, or other means with the understanding that the seal means effectively allows the sterile liquid perfluorocarbon material (17) within the barrel (11) to remain sterile until such time as the means is removed. At the distal-most end of the barrel is a second seal means (16) fixedly positioned at the distal-most end of the barrel and which is preferably made of rubber or rubber-like material easily puncturable by a hypodermic needle (18), and yet constructed in such a manner as to seal the liquid contents (17) within the barrel in such a manner as to render the seal liquid tight and the maintain the liquid contents in an aseptic condition.

Figure 1:
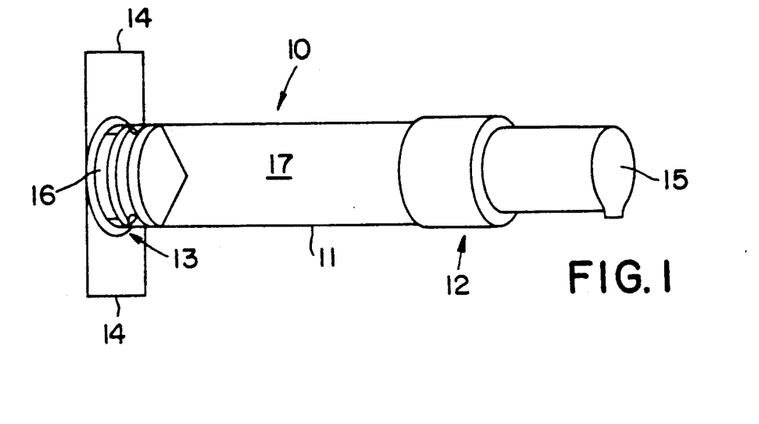
FIG. 1 shows a perspective view of a sealed apparatus according to one aspect of the present invention.
Figure 2:
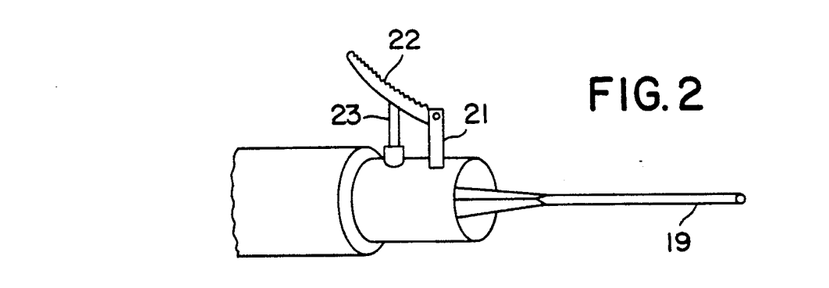
FIG. 2 shows a one-quarter perspective view of the proximal end of the apparatus shown in FIG. 1.
Figure 3:
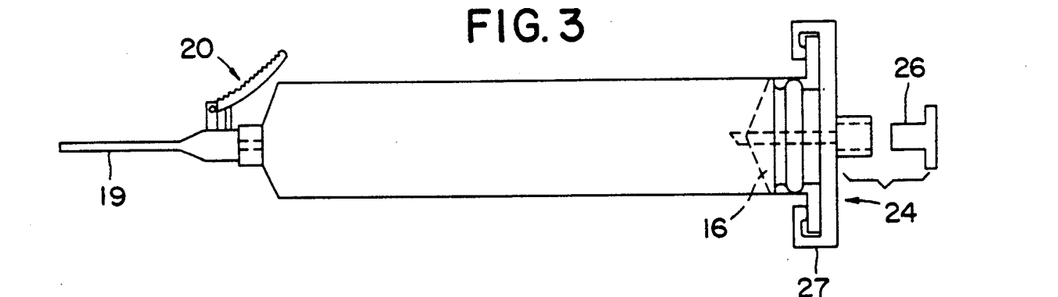
FIG. 3 shows a lateral plan view of an assembled apparatus according to another aspect of the present invention.

Carried either on the proximal end (12) of the barrel (11) or at the distal end of dispensing canula (19), the actual site being dictated by manufacturing and design choice, is a control and metering valve (20) which comprises a support rod (21), a lever (22) and a valve release rod (23). In operation, when the surgeon depresses the control lever (22) the valve release rod (23) is depressed allowing the flow of the liquid perfluorocarbon through the canula (19) at the infusion pressure set on the air pump attached to distal clamp (24). As conventional surgical technique suggests the opening into the eye is about 20 gauge, canula (19) is preferably chosen to be 33 gauge blunt hypodermic needle. The smaller sized hypodermic needle on the canula allows some leakage around the sclerotomy during the injection of liquid perfluorocarbon reducing the possibility of severe rises in intraocular pressure and the concurrent possibility of causing reflux into the dispensing needle.

Figure 4:
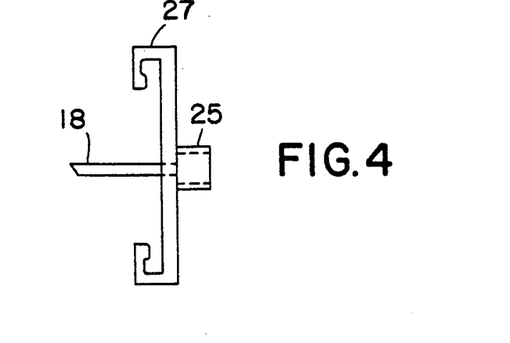
FIG. 4 shows a lateral plan view of the distal clamp of the apparatus according to the present invention.

At the distal end of the barrel (11) is the pumping clamp (24 carrying an anterior positioned hypodermic needle (18) adapted to puncture the rear seal means (16) of the apparatus, and a female posterior air port (25) whose interior opening is axial to and communicates with the interior passageway of needle (18). Although the air port (25) is shown in FIGS. 3 and 4 as being adapted to carry a friction-fit with a male port (26) which is attached to an air supply line, the design of these ports may be varied according to accepted design parameters. In use, the air supply line is inserted or otherwise attached to the pumping clamp (24), the clamp is attached to the barrel (11) by pushing the hypodermic needle (18) through the posterior seal (16). Once the needle passes through the seal means, the clamp is pivoted until overlapping tabs (27) carried by the clamp overlap the flange portions (14) carried by the syringe body. Tabs (27) are so designed so as to firmly grip and hold the clamp (24) until the assembled apparatus.

In use, the instrument will be attached to a filtered air supply set to deliver air at a pressure of about 25 to 30 mm Hg to the instrument. Control of the amount of perfluorocarbon dispensed will be with the surgeon who, rather than an assistant, will be able to control the finger valve allowing the fluid to flow into the eye. Furthermore, since the surgeon is the one holding the instrument, minimal displacement of the needle will occur during injection.

The terms and expressions which have been employed in the foregoing specification are sued therein as the terms of description and not of limitation, and there is no intention, in the use of such terms and expressions, of excluding equivalents of the features shown and described or portions thereof, it being recognized that the scope of the invention is defined and limited only by the claims which follow.

Thus, while I have illustrated and described the preferred embodiment of my invention, it is to be understood that this invention is capable of variation and modification, and I therefore do not wish or intend to be limited to the precise terms set forth, but desire and intend to avail myself of such changes and alterations which may be made for adapting the invention of the present invention to various usages and conditions. Accordingly, such changes and alterations are properly intended to be within the full range of equivalents, and therefore within the purview, of the following claims.

Having thus described my invention and the manner and process of making and using it in such full, clear, concise, and exact terms so as to enable any person skilled in the art to which it pertains, or with which it is most nearly connected, to make and use the same:

I claim:

1. A surgical procedure for the hydrokinetic manipulation of the retina during vitreous surgery for retinal detachment which comprises:
   making at least one incision in the pars plana of the eye to gain entry to the vitreous chamber of the eye;
   removing at least a portion of the vitreous from the vitreous chamber;
   infusing a sufficient amount of a liquid perfluorocarbon into the vitreous chamber of the eye to stabilize the retina and provide for manipulation of the retina;
   manipulating the retina into substantially its normal position within the eye;
   repairing the retinal detachment; and
   removing the liquid perfluorocarbon from the vitreous chamber of the eye.

2. The procedure according to claim 1 wherein the infusing of liquid perfluorocarbon into the chamber of the eye continues until from about 5 to about 85 percent of the chamber becomes filled with the perfluorocarbon.

3. A procedure according to claim 1 which further comprises removing a least a portion of the vitreous in the chamber of the eye prior to infusion with perfluorocarbon.

4. The procedure according to claim 1 which further comprises introducing a sterile gas bubble or silicon oil into the eye chamber as a long term vitreous replacement.

5. A procedure according to claim 1 wherein the liquid perfluorocarbon is removed from the chamber of the eye by aspiration.

6. The procedure according to claim 1 wherein the removal of liquid perfluorocarbon from the chamber of the eye comprises:
   introducing saline into the chamber of the eye and thereby causing any residual amounts of perfluorocarbon to coalesce into spheres; and
   removing the spherical perfluorocarbon from the the chamber by aspiration.

7. A surgical procedure for the hydrokinetic manipulation of the retina during vitreous surgery for retinal detachment which comprises:
   making at least one incision in the pars plana of the eye to gain entry to the vitreous chamber of the eye;
   infusing a sufficient amount of a liquid perfluorocarbon into the vitreous chamber of the eye to stabilize the retina and provide for manipulation of the retina;
   manipulating the retina into substantially its normal position within the eye;
   repairing the retinal detachment;
   introducing saline into the chamber thereby causing any residual amounts perfluorocarbon to coalesce into spheres; and
   removing the liquid perfluorocarbon from the vitreous chamber of the eye by aspiration.

8. In a surgical procedure for the surgical repair of retinal detachment require requires the manipulation of the retina by the surgeon, the improvement of which comprises removing at least a portion of the vitreous from the chamber of the eye and infusing over the optic disk an amount of liquid perfluorocarbon sufficient to provide for intraoperative hydrokinetic manipulation of the retina by the surgeon.

9. A surgical procedure for the hydrokinetic manipulation of the retina during vitreous surgery for retinal detachment which comprises:

making at least one incision in the pars plana of the eye to gain entry to the vitreous chamber of the eye;

removing at least a portion of the vitreous from the vitreous chamber;

infusing a sufficient amount of a liquid, optically clear perfluorocarbon having a specific gravity of from about 1.3 to about 2.1 and a refractive index of from about 1.25 to about 1.34 into the vitreous chamber of the eye to stabilize the retina and provide for manipulation of the retina;

manipulating the retina into substantially its normal position within the eye;

repairing the retinal detachment; and removing the liquid perfluorocarbon from the vitreous chamber of the eye.

10. A surgical procedure for the hydrokinetic manipulation of the retina during vitreous surgery for retinal detachment brought about by diabetic retinopathy, proliferative retinopathy, retinopathy of prematurity, retinal tearing, or ocular trauma which comprises:

making at least one incision in the pars plana of the eye to gain entry to the vitreous chamber of the eye;

removing at least a portion of the vitreous from the vitreous chamber;

infusing a sufficient amount of a liquid perfluorocarbon into the vitreous chamber of the eye to stabilize the retina and provide for manipulation of the retina;

manipulating the retina into substantially its normal position within the eye;

repairing the retinal detachment; and removing the liquid perfluorocarbon from the vitreous chamber of the eye.

* * * * *

REEXAMINATION CERTIFICATE (2357th)

United States Patent [19]

Chang

[11] B1 5,037,384

[45] Certificate Issued Aug. 16, 1994

[54] METHOD AND APPARATUS FOR THE TREATMENT OF COMPLICATED RETINAL DETACHMENTS

[75] Inventor: Stanley Chang, Scarsdale, N.Y.

[73] Assignee: Cornell Research Foundation, Inc., Ithaca, N.Y.

Reexamination Request:
No. 90/002,481, Oct. 17, 1991

Reexamination Certificate for:
Patent No.: 5,037,384
Issued: Aug. 6, 1991
Appl. No.: 405,615
Filed: Sep. 11, 1989

Related U.S. Application Data

[63] Continuation of Ser. No. 142,614, Jan. 12, 1988, abandoned.

[51] Int. Cl.$^5$ .............................................. A61M 1/00
[52] U.S. Cl. ............................................ 604/28; 604/49

[56] References Cited

U.S. PATENT DOCUMENTS 4,490,351  12/1984  Clark ....................................... 424/5

OTHER PUBLICATIONS

"Low Viscosity Liquid Fluorochemicals in Vitreous Surgery", Stanley Chang, *American Journal of Ophthalmology* vol. 103, No. 1, pp. 38–43, Jan. 15, 1987.

Chang, Stanley, M. D. et al; "Experimental Vitreous Replacement With Perfluorotributylamine"; *American Journal of Ophthalmology* 103:29–37, Jan. 1987.

Zimmerman, Neal J. et al; "The Use of N-Perfluorocarbon Amines in Complicated Retinal Detachments"; ARVO Abstracts; Supplement to Investigative Ophthalmology & Visual Science: vol. 25, No. 3, Mar. 1984, p. 258.

*Primary Examiner*—Michael H. Thaler

[57] ABSTRACT

The present invention relates to an improved microsurgical instrumentation, and an improved method using a perfluorocarbon material for hydrokinetic manipulation, for the surgical treatment of complicated retinal detachments of the eye.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 4–7 having been finally determined to be unpatentable, are cancelled.

Claims 1 and 8–10 are determined to be patentable as amended.

Claims 2–3, dependent on an amended claim, are determined to be patentable.

New claims 11–13 are added and determined to be patentable.

1. A surgical procedure for the hydrokinetic manipulation of the retina during vitreous surgery for retinal detachment which comprises:
   making at least one incision in the pars plana of the eye to gain entry to the vitreous chamber of the eye;
   removing at least a portion of the vitreous from the vitreous chamber;
   infusing a sufficient amount of a liquid perfluorocarbon into the vitreous chamber of the eye to stabilize the retina and provide for manipulation of the retina;
   manipulating the retina into substantially its normal position within the eye;
   repairing the retinal detachment; [and]
   *introducing silicone oil into the vitreous chamber of the eye as a long term vitreous replacement, and*
   *concurrently with said introduction of silicone oil into said chamber removing the liquid perfluorocarbon from the vitreous chamber of the eye.*

8. In a surgical procedure for the surgical repair of retinal detachment [require] *which* requires the manipulation of the retina by the surgeon, the improvement of which comprises removing at least a portion of the vitreous from the chamber of the eye [and], infusing over the optic disk an amount of liquid perfluorocarbon sufficient to provide for intraoperative hydrokinetic manipulation of the retina by the surgeon, *and removing the liquid perfluorocarbon from the vitreous chamber of the eye concurrently with the introduction of silicone oil into the eye chamber as a long term vitreous replacement.*

9. A surgical procedure for the hydrokinetic manipulation of the retina during vitreous surgery for retinal detachment which comprises:
   making at least one incision in the pars plana of the eye to gain entry to the vitreous chamber of the eye;
   removing at least a portion of the vitreous from the vitreous chamber;
   infusing a sufficient amount of a liquid, optically clear perfluorocarbon having a specific gravity of from 1.3 to about 2.1 and a refractive index of from about 1.25 to about 1.34 into the vitreous chamber of the eye to stabilize the retina and provide for manipulation of the retina;
   manipulating the retina into substantially its normal position within the eye;
   repairing the retinal detachment; [and]
   *introducing silicone oil into the vitreous chamber of the eye as a long term vitreous replacement, and*
   *concurrently with said introduction of silicone oil into said chamber removing the liquid perfluorocarbon from the vitreous chamber of the eye.*

10. A surgical procedure for the hydrokinetic manipulation of the retina during vitreous surgery for retinal detachment brought about by diabetic retinopathy, poliferative retinopathy, retinopathy of prematurely, retinal tearing, or ocular trauma which comprises:
    making at least one incision in the pars plana of the eye to gain entry to the vitreous chamber of the eye;
    removing at least a portion of the vitreous from the vitreous chamber;
    infusing a sufficient amount of a liquid into the vitreous chamber of the eye to stabilize the retina and provide for manipulation of the retina;
    manipulating the retina into substantially its normal position within the eye;
    repairing the retinal detachment; [and]
    *introducing silicone oil into the vitreous chamber of the eye as a long term vitreous replacement, and*
    *concurrently with said introduction of silicone oil into said chamber removing the liquid perfluorocarbon from the vitreous chamber of the eye.*

*11. A surgical procedure for the hydrokinetic manipulation of the retina during vitreous surgery for retinal detachment which comprises:*
   *making at least one incision in the pars plana of the eye to gain entry to the vitreous chamber of the eye;*
   *removing at least a portion of the vitreous from the vitreous chamber;*
   *infusing a sufficient amount of a perfluorocarbon comprised of perfluorooctane in a liquid state into the vitreous chamber of the eye to stabilize the retina and provide for manipulation of the retina;*
   *manipulting the retina into substantially its normal position within the eye;*
   *repairing the retinal detachment; and*
   *removing said perfluorocarbon by aspirating in conjunction with the introduction of a sterile gas bubble as a long term vitreous replacement.*

*12. The procedure according to claim 11 wherein the infusing of liquid perfluorocarbon into the chamber of the eye continues until from about 5 to about 85 percent of the chamber becomes filled with the perfluorocarbon.*

*13. The procedure according to claim 11 which further comprises removing at least a portion of the vitreous in the chamber of the eye prior to infusion with perfluorocarbon.*

* * * * *

REEXAMINATION CERTIFICATE (2757th)
United States Patent [19]
Chang

[11] B1 5,037,384
[45] Certificate Issued  Dec. 26, 1995

[54] METHOD AND APPARATUS FOR THE TREATMENT OF COMPLICATED RETINAL DETACHMENTS

[75] Inventor: Stanley Chang, Scarsdale, N.Y.

[73] Assignee: Cornell Research Foundation, Inc., Ithaca, N.Y.

Reexamination Requests:
 No. 90/003,524, Aug. 8, 1994

Reexamination Certificate for:
 Patent No.: 5,037,384
 Issued: Aug. 6, 1991
 Appl. No.: 405,615
 Filed: Sep. 11, 1989

Reexamination Certificate B1 5,037,384 issued Aug. 16, 1994

Related U.S. Application Data

[63] Continuation of Ser. No. 142,614, Jan. 12, 1988, abandoned.
[51] Int. Cl.$^6$ .................................................. A61M 1/00
[52] U.S. Cl. .................................. 604/28; 604/49
[58] Field of Search .................................. 604/28

[56] References Cited

PUBLICATIONS

Michels, R. G.; "Vitrectomy Techniques in Retinal Reattachment Surgery", *Opthalmology*, 86:556–585 (1979).
Michels, R. G.; "Vitreous Surgery", CV Mosby Company, 1981, pp. 180, 181, 184.
Leaver, P. K.; and Lean, J. S.; "Management of Giant Retinal Tears Using Vitrectomy and Silicone Oil Fluid Exchange", *Trans. Opthalmol Soc. U.K.* 101:189–191 (1981).
Lean, J. S.; Leaver, P. K.; Cooling, R. J.; and McCleod, D.; "Management of Complex Retinal Detachments by Vitrectomy and Fluid/Silicone Exchange", *Trans. Opthalmol. Soc. U.K.* 102:203–205 (1982).
McCleod, D.; "Silicone–Oil Injection During Closed Microsurgery for Diabetic Retinal Detachment", *Graefe's Arch. Clin. Exp. Opthalmol.* 224:55–59 (1986).
Peyman, G. A.; and Schulman, J. A.; "Intravitreal Surgery", Appleton–Century–Kroffs, 1986, pp. 316–317.

*Primary Examiner*—Michael H. Thaler

[57] ABSTRACT

The present invention relates to an improved microsurgical instrumentation, and an improved method using a perfluorocarbon material for hydrokinetic manipulation, for the surgical treatment of complicated retinal detachments of the eye.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–3 and 8–13 is confirmed.

Claims 4–7 were previously cancelled.

* * * * *